(12) United States Patent
Nakano

(10) Patent No.: US 10,379,232 B2
(45) Date of Patent: Aug. 13, 2019

(54) RADIATION IMAGE CAPTURING SYSTEM

(71) Applicant: KONICA MINOLTA, INC., Chiyoda-ku, Tokyo (JP)

(72) Inventor: Hiroaki Nakano, Sagamihara (JP)

(73) Assignee: KONICA MINOLTA, INC., Tokyo (JP)

( * ) Notice: Subject to any disclaimer, the term of this patent is extended or adjusted under 35 U.S.C. 154(b) by 44 days.

(21) Appl. No.: 15/467,742

(22) Filed: Mar. 23, 2017

(65) Prior Publication Data
US 2017/0299736 A1  Oct. 19, 2017

(30) Foreign Application Priority Data
Apr. 13, 2016  (JP) .................. 2016-079963

(51) Int. Cl.
*G01T 1/17* (2006.01)
*G01T 7/00* (2006.01)
*A61B 6/00* (2006.01)

(52) U.S. Cl.
CPC .............. *G01T 7/00* (2013.01); *A61B 6/4233* (2013.01); *A61B 6/4283* (2013.01); *A61B 6/4411* (2013.01); *A61B 6/4494* (2013.01); *G01T 1/17* (2013.01); *A61B 6/54* (2013.01); *A61B 6/56* (2013.01)

(58) Field of Classification Search
CPC ..................................... G01T 7/00; G01T 1/17
See application file for complete search history.

(56) References Cited

U.S. PATENT DOCUMENTS

| | | | | |
|---|---|---|---|---|
| 6,431,751 B1 * | 8/2002 | Everett | ............... | A61B 6/4233 378/193 |
| 7,193,219 B2 * | 3/2007 | Schick | ............... | A61B 5/0088 250/370.11 |
| 7,239,685 B2 * | 7/2007 | Petrick | ............... | G01T 1/2985 378/116 |
| 7,751,529 B2 * | 7/2010 | Ohara | ............... | A61B 6/00 378/116 |
| 8,172,461 B2 * | 5/2012 | Liu | ............... | A61B 6/4283 378/114 |

(Continued)

FOREIGN PATENT DOCUMENTS

JP   2002336225 A   11/2002
WO   2011048868 A1   4/2011

*Primary Examiner* — David P Porta
*Assistant Examiner* — Djura Malevic
(74) *Attorney, Agent, or Firm* — Holtz, Holtz & Volek PC

(57) ABSTRACT

A radiation image capturing system including: a radiation image capturing apparatus which is portable and reads emitted radiation as image data; and a plurality of consoles, wherein when the radiation image capturing apparatus is attached to an attachment section which is associated with one console among the plurality of consoles, the one console determines whether the radiation image capturing apparatus is registrable, and when the one console determines that the radiation image capturing apparatus is registrable, the one console registers the radiation image capturing apparatus, and in a case where the radiation image capturing apparatus is already registered in another console among the plurality of consoles, the another console cancels registration of the radiation image capturing apparatus only when the one console registers the radiation image capturing apparatus.

4 Claims, 6 Drawing Sheets

(56) References Cited

U.S. PATENT DOCUMENTS

| | | | |
|---|---|---|---|
| 8,295,439 B2 * | 10/2012 | Yonekawa | A61B 6/00 378/115 |
| 8,705,700 B2 * | 4/2014 | Eguchi | A61B 6/4233 378/116 |
| 9,186,118 B2 * | 11/2015 | Yonekawa | A61B 6/4233 |
| 9,289,182 B2 * | 3/2016 | Yonekawa | A61B 6/4233 |
| 9,366,766 B2 * | 6/2016 | Okada | H04N 5/32 |
| 9,405,183 B2 * | 8/2016 | Ando | A61B 6/4266 |
| 9,453,923 B2 * | 9/2016 | Eguchi | A61B 6/4233 |
| 9,513,379 B2 * | 12/2016 | Nishino | A61B 6/548 |
| 9,952,335 B2 * | 4/2018 | Okada | H04N 5/32 |
| 9,968,327 B2 * | 5/2018 | Chen | A61B 6/4208 |
| 2002/0090055 A1 * | 7/2002 | Zur | G21K 1/02 378/154 |
| 2005/0043620 A1 * | 2/2005 | Fallows | A61B 8/14 600/437 |
| 2006/0016998 A1 * | 1/2006 | Ohara | G01T 1/2018 250/370.11 |
| 2006/0054822 A1 * | 3/2006 | Tsuchino | G01T 1/2018 250/336.1 |
| 2006/0188071 A1 * | 8/2006 | Spahn | A61B 6/4283 378/196 |
| 2007/0045552 A1 * | 3/2007 | Masazumi | G01T 1/24 250/370.09 |
| 2009/0022276 A1 * | 1/2009 | Ohara | A61B 6/00 378/101 |
| 2009/0028295 A1 * | 1/2009 | Ohta | A61B 6/4233 378/98 |
| 2009/0189761 A1 * | 7/2009 | Nishino | A61B 6/00 340/540 |
| 2009/0279764 A1 * | 11/2009 | Kaji | A61B 6/00 382/132 |
| 2011/0026676 A1 * | 2/2011 | Takekoshi | A61B 6/06 378/98.2 |
| 2011/0110494 A1 * | 5/2011 | Lee | G03B 42/04 378/98 |
| 2011/0317809 A1 * | 12/2011 | Eguchi | A61B 6/4233 378/62 |
| 2012/0207278 A1 * | 8/2012 | Yonekawa | A61B 6/4233 378/98.5 |
| 2012/0286167 A1 * | 11/2012 | Eguchi | A61B 6/00 250/393 |
| 2013/0038738 A1 * | 2/2013 | Ando | A61B 6/4266 348/162 |
| 2014/0241503 A1 * | 8/2014 | Yonekawa | A61B 6/4233 378/62 |

* cited by examiner

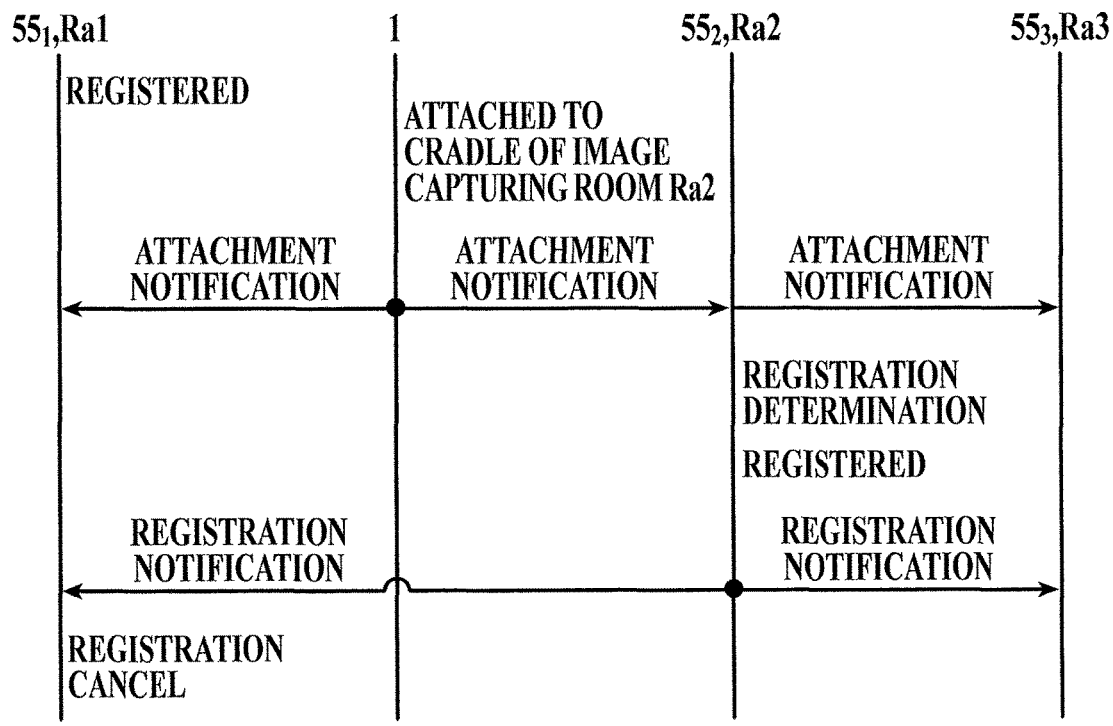
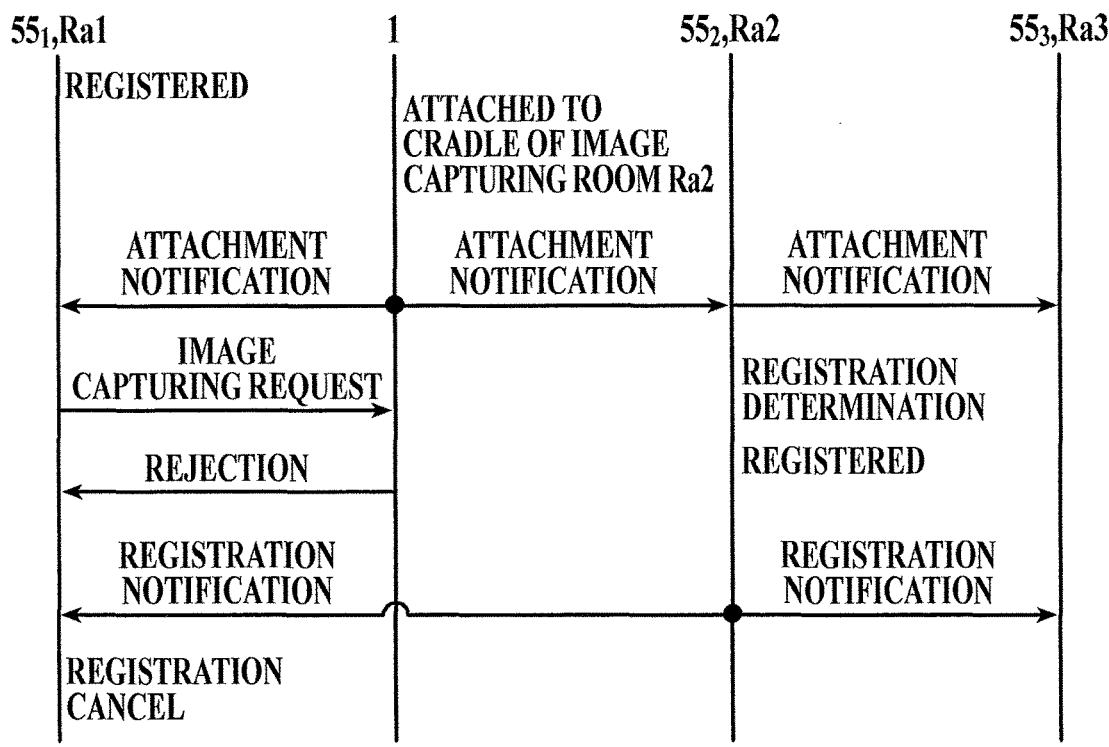

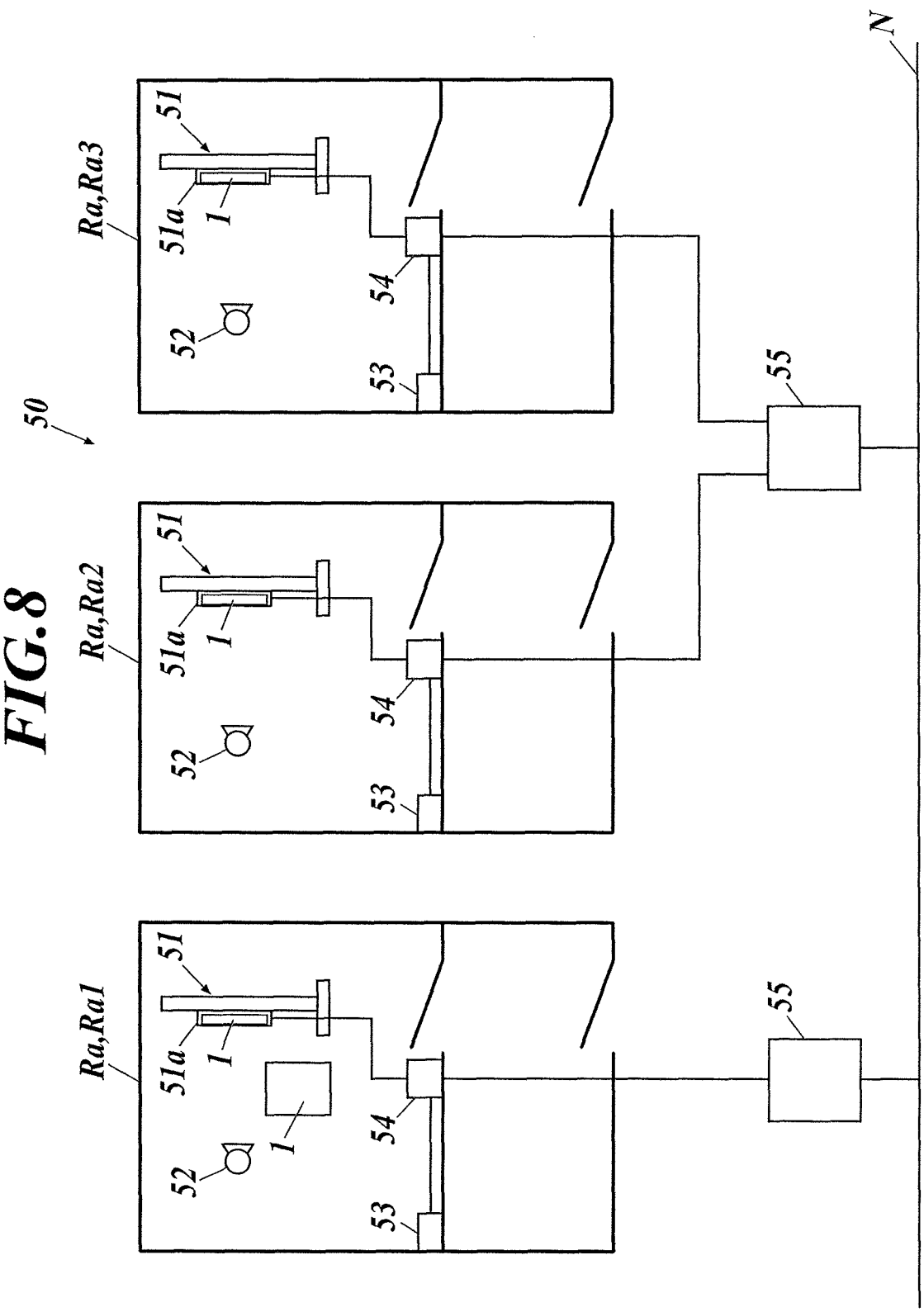

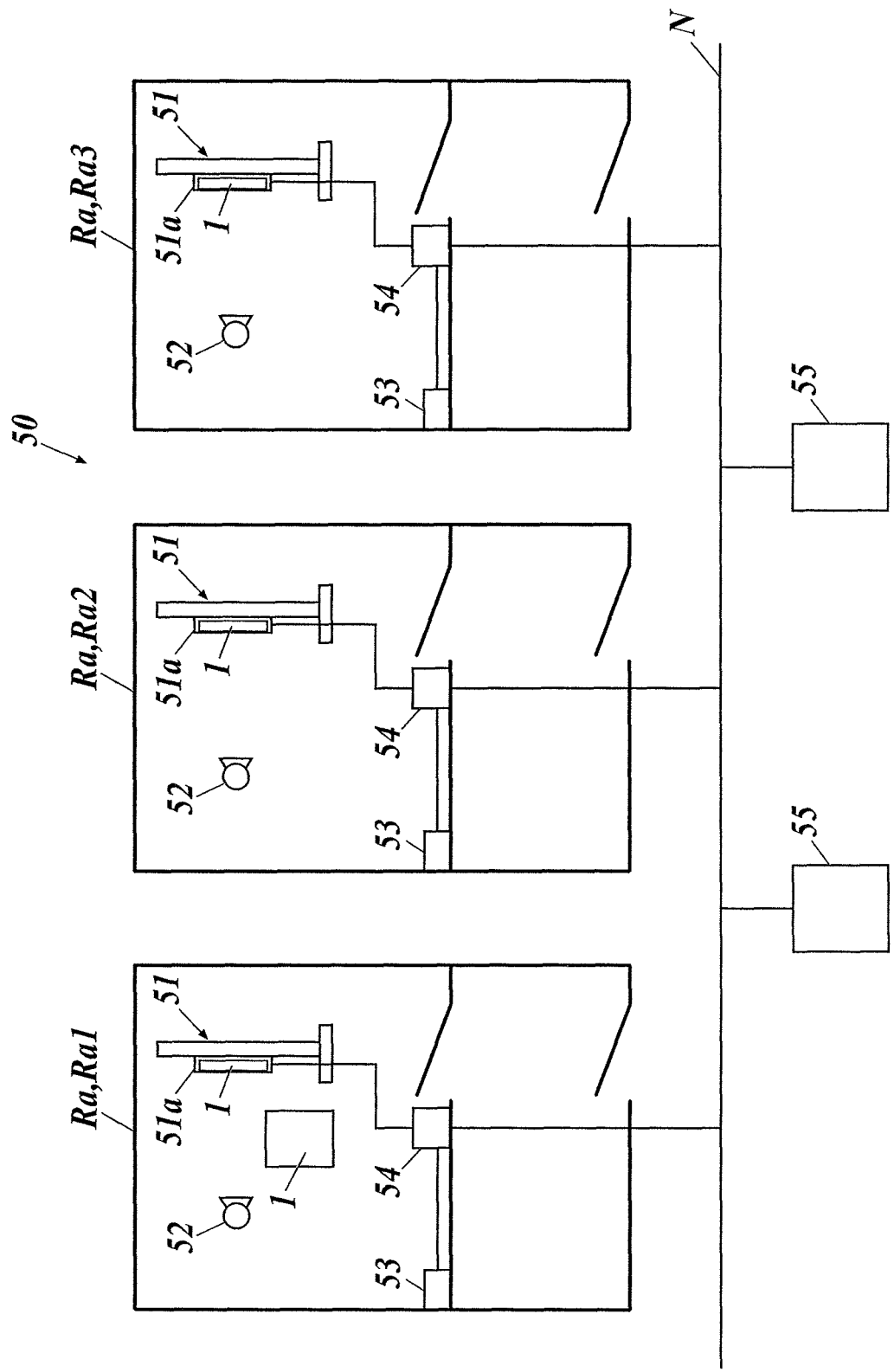

RADIATION IMAGE CAPTURING SYSTEM

CROSS-REFERENCE TO RELATED APPLICATIONS

The entire disclosure of Japanese Patent Application No. 2016-079963 filed on Apr. 13, 2016 including description, claims, drawings and abstract are incorporated herein by reference in its entirety.

BACKGROUND OF THE INVENTION

1. Field of the Invention

The present invention relates to a radiation image capturing system, especially a radiation image capturing system which is capable of image capturing in a plurality of image capturing rooms by using a radiation image capturing apparatus.

2. Description of Related Art

There have been developed various radiation image capturing apparatuses (Flat Panel Detectors) which generate electric charges in a plurality of radiation detection elements according to the dose of emitted radiation and read the generated electric charges as image data. In recent years, there have been also developed portable radiation image capturing apparatuses which are formed to be cassette types and portable.

In facilities such as a hospital having a plurality of image capturing rooms, there are some cases where a portable radiation image capturing apparatus (hereinafter, simply referred to as a radiation image capturing apparatus) is carried from one image capturing room to another image capturing room to perform image capturing. In such a case, it is necessary to appropriately manage in which image capturing room the radiation image capturing apparatus is located, otherwise there occur problems that a radiological technician or the like needs to rotate through each image capturing room to find an intended radiation image capturing apparatus, or image capturing cannot be appropriately performed due to the use of a radiation image capturing apparatus which is different from the radiation image capturing apparatus that was supposed to be used.

Thus, in a radiation image capturing system described in International Publication No. 2011/048868, for example, a cradle is provided in each image capturing room, and when a radiological technician carries a radiation image capturing apparatus into an image capturing room and attaches the radiation image capturing apparatus to the cradle, the radiation image capturing apparatus is registered. When the registration processing is performed in such a way, identification information or the like of the radiation image capturing apparatus is notified to a management apparatus, and the management apparatus associates the identification information of the radiation image capturing apparatus with identification information of the image capturing room, and manages in which image capturing room the radiation image capturing apparatus is located. In a case where the radiation image capturing apparatus is already associated with another image capturing room, the management apparatus cancels the association to cancel the registration of the radiation image capturing apparatus with respect to the original image capturing room (image capturing room where the radiation image capturing apparatus was located before movement).

In addition, Japanese Patent Application Laid Open Publication No. 2002-336225 discloses an invention of a radiation image capturing system including an image capturing stand which has a holding section to hold a radiation image capturing apparatus so as to be detachable, and a control apparatus which operates on the basis of system information specifying an image capturing system that is formed by a combination of the radiation image capturing apparatus and the holding section of the image capturing stand. The control apparatus is configured to prohibit operation related to image capturing when the actual combination is not consistent with the combination which was specified in advance.

In the above-mentioned radiation image capturing system described in International Publication No. 2011/048868, the location of radiation image capturing apparatus is collectively managed by the management apparatus. However, in a case of managing the location by a console provided in each image capturing room, for example, the following problem occurs. The same problem also occurs in the radiation image capturing system described in Japanese Patent Application Laid Open Publication No. 2002-336225.

That is, for example, in a case where the radiation image capturing apparatus is carried into another image capturing room from the original image capturing room and attached to the cradle or the like to be registered, the registration possibly fails due to a bad communication environment, an abnormality of the console, licensing violation or the like. Furthermore, in the system described in Japanese Patent Application Laid Open Publication No. 2002-336225, when the carried radiation image capturing apparatus is fixed into the holding section of the image capturing stand, image capturing is possibly prohibited due to inconsistency between the specified combination and the combination of the radiation image capturing apparatus and the holding section.

In such a situation, for example, when the information that the radiation image capturing apparatus was registered in another image capturing room is notified to the console of the original image capturing room and the console of the original image capturing room cancels the association of the radiation image capturing apparatus to cancel the registration, the radiation image capturing apparatus is not registered in the original image capturing room nor in the another image capturing room. Thus, it is possibly regarded that the radiation image capturing apparatus does not exist in the original image capturing room nor in the another image capturing room.

SUMMARY OF THE INVENTION

The present invention has been made in consideration of the above problems, and an object of the present invention is to provide a radiation image capturing system which is capable of accurately performing registration and registration cancel of the radiation image capturing apparatus in each console when the radiation image capturing apparatus is carried to be used.

In order to solve at least one of the above problems, according to one aspect of the present invention, there is provided a radiation image capturing system including: a radiation image capturing apparatus which is portable and reads emitted radiation as image data; and a plurality of consoles, wherein when the radiation image capturing apparatus is attached to an attachment section which is associated with one console among the plurality of consoles, the one console determines whether the radiation image capturing apparatus is registrable, and when the one console determines that the radiation image capturing apparatus is registrable, the one console registers the radiation image capturing apparatus, and in a case where the radiation image capturing apparatus is already registered in another console among the plurality of consoles, the another console cancels registration of the radiation image capturing apparatus only when the one console registers the radiation image capturing apparatus.

BRIEF DESCRIPTION OF THE DRAWINGS

The above and other objects, advantages and features of the present invention will become more fully understood from the detailed description given hereinafter and the appended drawings which are given by way of illustration only, and thus are not intended as a definition of the limits of the present invention, and wherein:

FIG. 6 is a view showing the flow of signals and the flow of processing performed in each console when the radiation image capturing apparatus is attached to a cradle in an image capturing room Ra2;

FIG. 7 is a view showing that, when an image capturing request is transmitted during registration processing, the radiation image capturing apparatus rejects the request and prohibits the image capturing;

FIG. 8 is a view showing another configuration example of a radiation image capturing system according to the embodiment; and FIG. 9 is a view showing another configuration example of a radiation image capturing system according to the embodiment.

DETAILED DESCRIPTION OF THE PREFERRED EMBODIMENT

Hereinafter, an embodiment of a radiation image capturing system according to the present invention will be described with reference to the drawings.

Figure 1:
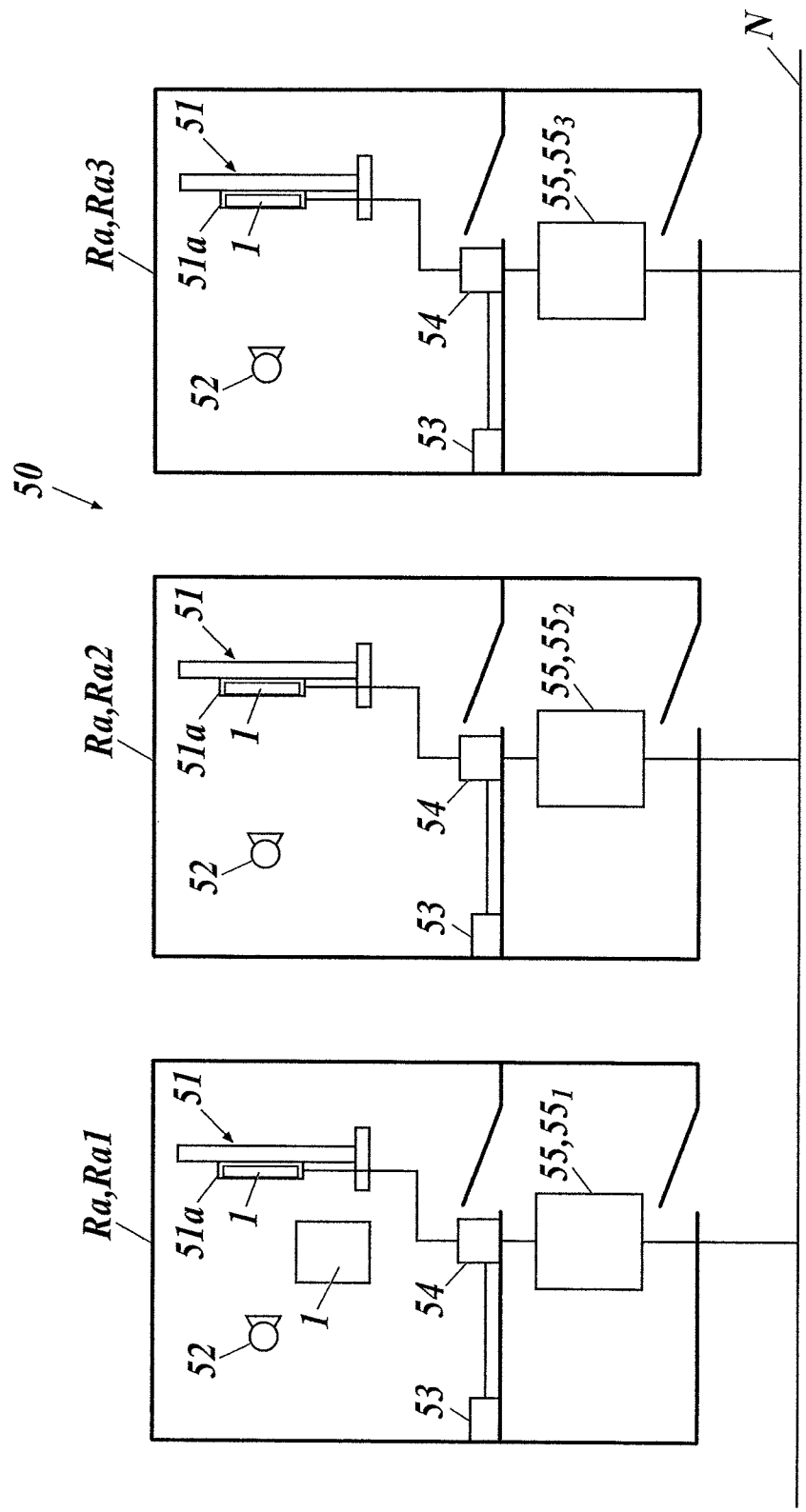
FIG. 1 is a view showing a configuration example of a radiation image capturing system according to an embodiment.

As shown in FIG. 1, for example, a radiation image capturing system 50 according to the embodiment includes a portable radiation image capturing apparatus 1 (hereinafter, simply referred to as a radiation image capturing apparatus 1) and a plurality of image capturing rooms Ra (Ra1 to Ra3). In each of the image capturing rooms Ra, an image capturing stand 51, an irradiation apparatus 52 and a cradle 53 are provided, and the image capturing stand 51, irradiation apparatus 52 and cradle 53 are connected to a console 55 via a repeater 54. It goes without saying that the present invention is not limited to the case where there are three image capturing rooms Ra.

Figure 2:
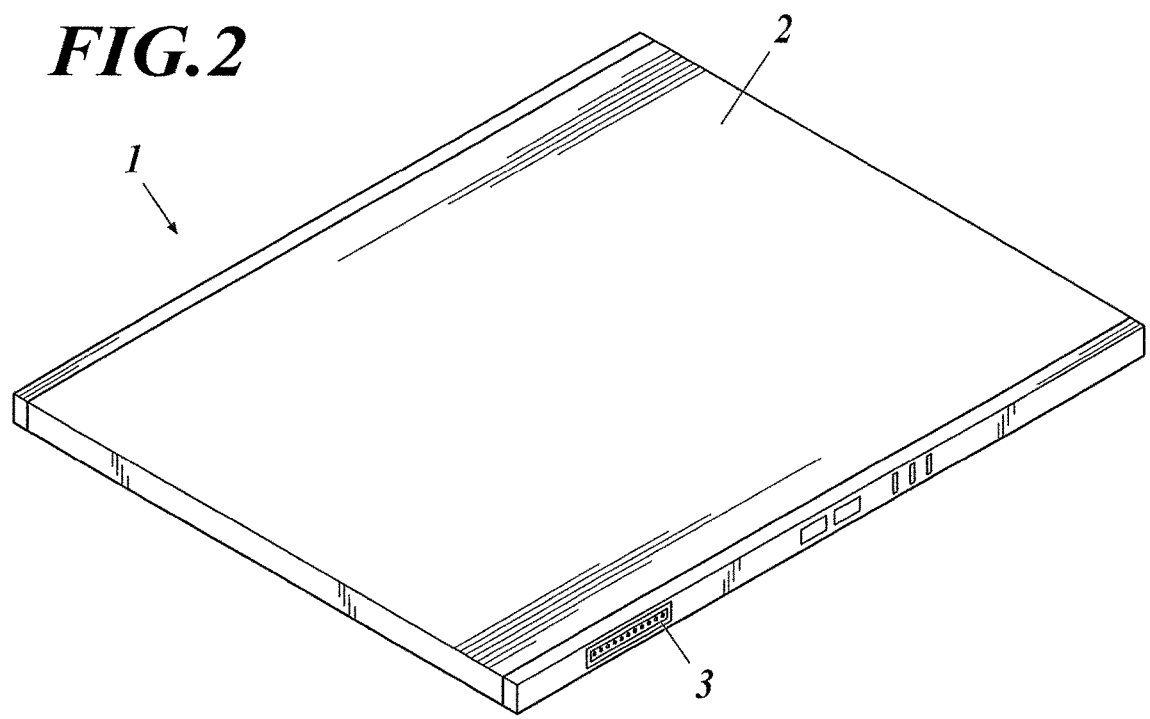
FIG. 2 is a perspective view showing the outer appearance of the radiation image capturing apparatus.

The radiation image capturing apparatus 1 is formed to be portable by including, in a housing 2 as shown in FIG. 2, a plurality of radiation elements (not shown in the drawings) which are arranged two dimensionally (in a matrix). When radiation is emitted from the irradiation apparatus 52 via a subject, the electric charges corresponding to the doze of the emitted radiation are generated in the radiation detection elements and the electric charges are read out as image data.

The radiation image capturing apparatus 1 can be used for image capturing by being fixed into a cassette holder (also referred to as a cassette holding section or the like) of the image capturing stand 51, or the radiation image capturing apparatus 1 can be independently used for image capturing by being put on a patient body which is the subject without being fixed into the image capturing stand 51.

Figure 3:
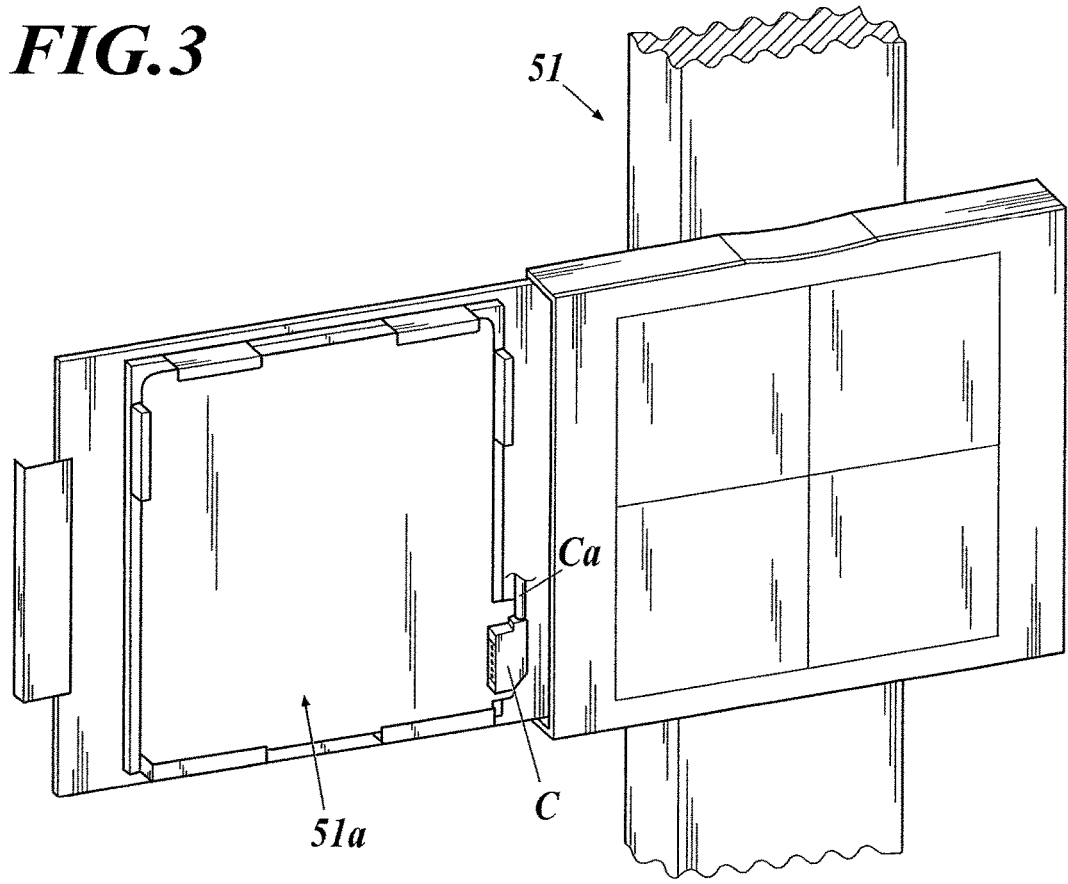
FIG. 3 is a view showing a configuration of an image capturing stand.

Though FIG. 1 shows an image capturing stand for upright image capturing as an image capturing stand 51, an image capturing table for recumbent image capturing may be provided. As shown in FIG. 3, the image capturing stand 51 includes a cable Ca having a connector C provided at the tip thereof. When the radiation image capturing apparatus 1 (not shown in FIG. 3) is fixed to a cassette holder 51a, the connector C of the image capturing stand 51 and a connector 3 (see FIG. 2) of the radiation image capturing apparatus 1 are attached to each other.

When the connector 3 is attached to the connector C of the image capturing stand 51, the radiation image capturing apparatus 1 reads identification information (hereinafter, referred to as a cable ID) of the cable Ca, transmits an attachment notification including identification information (hereinafter, referred to as a cassette ID) of the radiation image capturing apparatus 1 and the cable ID to the console 55 via the cable Ca and the repeater 54, and transmits the attachment notification to consoles 55 of the other image capturing rooms Ra via the console 55 and an after-mentioned communication network N.

That is, in the embodiment, the cable Ca of the image capturing stand 51 functions as one of attachment sections to which the radiation image capturing apparatus 1 is attached. The connector C of the cable Ca which is the attachment section may read the cassette ID of the radiation image capturing apparatus 1 and transmit the attachment notification including the cable ID and the cassette ID to each console 55.

Figure 4:
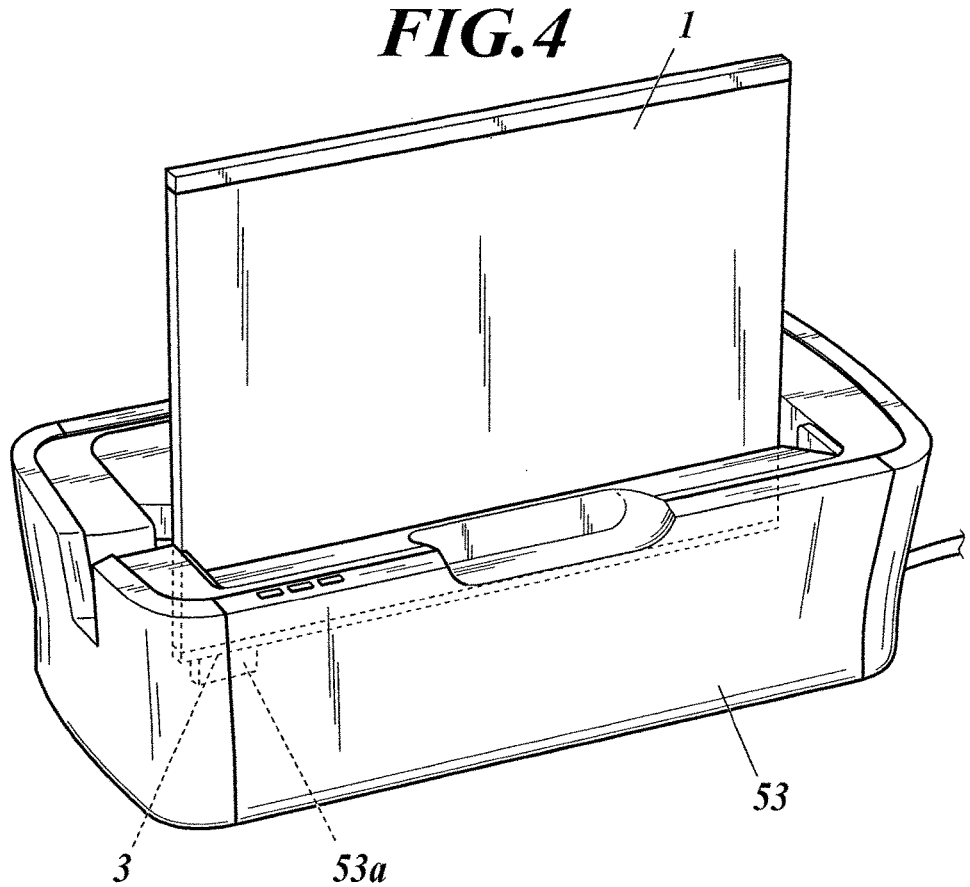
FIG. 4 is a view showing a state in which the radiation image capturing apparatus is attached to a cradle.

As shown in FIG. 1, the cradle 53 is connected to the repeater 54. As shown in FIG. 4, when the radiation image capturing apparatus 1 is attached to the cradle 53, the connector 3 of the radiation image capturing apparatus 1 is connected to a connector 53a which is provided in the cradle 53.

When the connector 3 is connected to the connector 53a of the cradle 53, the radiation image capturing apparatus 1 reads identification information (hereinafter, referred to as a cradle ID) of the cradle 53, and transmits an attachment notification including the cassette ID of the radiation image capturing apparatus 1 and the cradle ID to each console 55 via the repeater 54 and the communication network N.

That is, in the embodiment, the cradle 53 also functions as one of the attachment sections to which the radiation image capturing apparatus 1 is attached. Also in this case, the cradle 53 which is the attachment section may read the cassette ID of the radiation image capturing apparatus 1 and transmit the attachment notification including the cradle ID and the cassette ID to each console 55.

In the embodiment, the consoles 55 are associated with respective image capturing rooms Ra. Each of the consoles 55 is configured by including a computer in which a CPU (Central Processing Unit), a ROM (Read Only Memory), a RAM (Random Access Memory), an input output interface and such like (not shown in the drawings) are connected to each other via a bus. Each of the consoles 55 may be configured as a dedicated apparatus.

Each of the consoles 55 is connected to the other consoles 55 via the communication network N. Though not shown in the drawings, each of the consoles 55 includes a display section, an input section, a storage section and such like. The other devices such as a server and an imager and an external system such as an HIS (Hospital Information System), an RIS (Radiology Information System) and a PACS (Picture Archiving and Communication System) are connected to the communication network N, for example.

Next, a configuration of the radiation image capturing system 50 according to the embodiment will be described, the configuration being a configuration for accurately performing registration and registration cancel of the radiation image capturing apparatus 1 in the console 55 of each image capturing room Ra without generating problems which possibly occur in the above-mentioned conventional systems when the radiation image capturing apparatus 1 is carried to be used between a plurality of image capturing rooms Ra. The function of radiation image capturing system 50 according to the embodiment will be described together.

In the embodiment, (1) when a radiation image capturing apparatus 1 is attached to an attachment section (cradle 53, cable Ca of image capturing stand 51 or the like) associated with one image capturing room Ra, the console 55 associated with the one image capturing room Ra determines whether the radiation image capturing apparatus 1 is registrable. If the console 55 determines that the radiation image capturing apparatus 1 is registrable, the console 55 registers the radiation image capturing apparatus 1.

(2) In a case where the radiation image capturing apparatus 1 is already registered in a console 55 of another image capturing room Ra, the console 55 of the another image capturing room Ra cancels the registration of the radiation image capturing apparatus 1 only when the console 55 associated with the one image capturing room Ra registers the radiation image capturing apparatus 1. When the console 55 associated with the one image capturing room Ra does not register the radiation image capturing apparatus 1 (that is, does not determine that the radiation image capturing apparatus 1 is registrable), the console 55 of the another image capturing room Ra does not cancel the registration of the radiation image capturing apparatus 1.

(3) In a case where the radiation image capturing apparatus 1 is already registered in the console 55 associated with the one image capturing room Ra, when the console 55 does not determine that the radiation image capturing apparatus 1 is registrable, the console does not cancel the registration of the radiation image capturing apparatus 1.

Figure 5A:
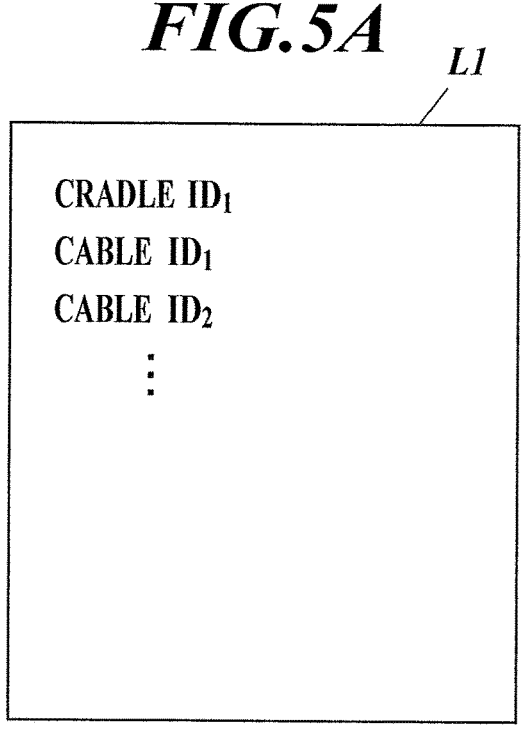
FIG. 5A is a view showing an example of a list of identification information of attachment sections which are associated with an image capturing room.

In the embodiment, as illustrated in FIG. 5A, each of the consoles 55 has a list L1 of identification information (that is, cradle IDs and cable IDs) of attachment sections (that is, cradles 53 and cables Ca) associated with the image capturing room Ra which is associated with the console 55. In this case, cradles 53 are set for respective image capturing rooms Ra and cables Ca are also basically not used commonly between a plurality of image capturing rooms Ra. Thus, the contents of the list L1 (cradle IDs, cable IDs and such like) are different between the consoles 55. In a case where a new attachment section is introduced into an image capturing room Ra, the identification information (cradle ID or cable ID) of the introduced attachment section is added to the list L1 of the console 55 associated with the image capturing room Ra.

In the embodiment, when an attachment notification including a cassette ID and a cradle ID or an attachment notification including a cassette ID and a cable ID is transmitted from the radiation image capturing apparatus 1 or the attachment section as described above, if the cradle ID or the cable ID belongs to the list L1, each of the consoles 55 determines that the radiation image capturing apparatus 1 is registrable. If the cradle ID or the cable ID does not belong to the list L1, each of the consoles 55 does not determine that the radiation image capturing apparatus is registrable.

By such configuration, each of the consoles 55 can easily and accurately determine whether the radiation image capturing apparatus 1 is registrable on the basis of the list L1 (that is, on the basis of whether the information of the attachment section belongs to the list L1).

Figure 5B:
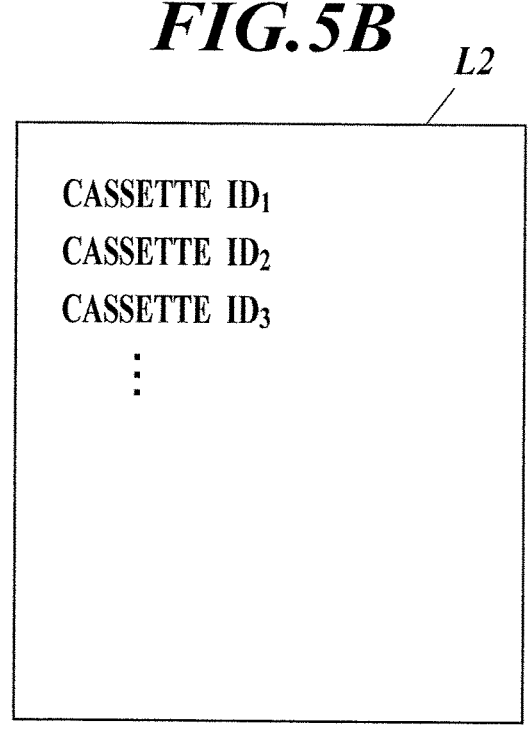
FIG. 5B is a view showing an example of a list of identification information of radiation image capturing apparatuses which can be used in a facility.

As shown in FIG. 5B, each of the consoles 55 has a list L2 (that is, a list L2 of cassette IDs of radiation image capturing apparatuses 1 having licenses, for example) of radiation image capturing apparatuses 1 which can be used in the facility such as the hospital (that is, in the radiation image capturing system 50). Each time a radiation image capturing apparatus 1 is newly introduced into the facility and the license thereof is registered, for example, the cassette ID of the radiation image capturing apparatus 1 is added to the list L2 and the list L2 is updated. The consoles 55 have the same list L2. Each of the consoles 55 may have a list including the lists L1 and L2 together.

For example, explanation is made for a case where the radiation image capturing apparatus 1 is carried out from the image capturing room Ra1, carried into the image capturing room Ra2 and attached to the cradle 53 (the same explanation is also applied to a case where the radiation image capturing apparatus 1 is attached to the cable Ca of the image capturing stand 51 or the like). In this case, as shown in FIG. 6, an attachment notification including the cassette ID and the cradle ID is transmitted to the console 55 of each of the image capturing rooms Ra1 to Ra3 from the radiation image capturing apparatus 1 or the cradle 53 as mentioned above.

When the attachment notification is received, each of the consoles 55 associated with the image capturing rooms Ra refers to the list L1 (see FIG. 5A) owned by the console 55, and determines whether the cradle ID included in the attachment notification belongs to the list L1. In a case of FIG. 6, the console 55 associated with the image capturing room Ra2 (hereinafter, referred to as the console $55_2$) determines that the received cradle ID belongs to the list L1.

Each of the consoles 55 (hereinafter, referred to as the consoles $55_1$ and $55_3$) associated with the image capturing rooms Ra1 and Ra3 determines that the received cradle ID does not belong to the list L1.

In this case, since the console $55_2$ is the "console 55 associated with the one image capturing room Ra" in the above (1), when the radiation image capturing apparatus 1 is attached to the cradle 53 which is the attachment section associated with the image capturing room Ra2, as shown in FIG. 6, the console $55_2$ determines whether the radiation image capturing apparatus 1 is registrable by referring to the above-mentioned list L2 (see FIG. 5B), for example.

If the cassette ID of the radiation image capturing apparatus 1 belongs to the list L2, the console $55_2$ determines that the radiation image capturing apparatus 1 is registrable and registers the radiation image capturing apparatus 1. At this time, the console $55_2$ performs the registration processing by writing the cassette ID of the radiation image capturing apparatus 1 into the list L1 or another list, for example. In either case, the list in which the cassette ID of the registered radiation image capturing apparatus 1 is written is hereinafter referred to as a registration list.

The list L2 illustrated in FIG. 5B is a list of radiation image capturing apparatuses 1 which can be used in a facility such as a hospital as mentioned above, and thus, each of the consoles 55 has the same list L2. On the other hand, the registration list is a list of the radiation image capturing apparatus 1 registered in each of the image capturing room Ra, and thus, the contents are different between the consoles 55. The radiation image capturing apparatus 1 registered in a registration list of a console 55 is not registered in the registration lists of the other consoles 55.

In the above case, when the cassette ID of the radiation image capturing apparatus 1 does not belong to the list L2 due to the license registration not being performed for the radiation image capturing apparatus 1, for example, the console $55_2$ does not write the cassette ID of the radiation image capturing apparatus 1 into the registration list (that is, does not register the radiation image capturing apparatus 1). The console $55_2$ notifies that the radiation image capturing apparatus 1 is not registered to a user such as a radiological technician by performing error display on the display section or generating sound, for example.

When the registration of the radiation image capturing apparatus 1 is completed in such a way (or at the time when it is determined that the radiation image capturing apparatus 1 is registrable), as shown in FIG. 6, the console $55_2$ transmits a registration notification accompanied with the cassette ID of the radiation image capturing apparatus 1 to the other consoles $55_1$ and $55_3$. The registration notification may be transmitted to each of the consoles $55_1$, $55_2$ and $55_3$ by the radiation image capturing apparatus 1 which received, from the console $55_2$, a notification indicating that the radiation image capturing apparatus 1 was registered (or a notification indicating that the radiation image capturing apparatus 1 is to be registered).

In the above case, the console $55_3$ associated with the image capturing room Ra3 is not the "console 55 associated with the one image capturing room Ra" in the above (1) and (3), and also not the "console 55 of another image capturing room Ra" of the "case where the radiation image capturing apparatus 1 is already registered in a console 55 of another image capturing room Ra" in the above (2). Thus, no processing is performed even when the console $55_3$ receives the attachment notification and the registration notification.

On the other hand, in the above case, the console $55_1$ associated with the image capturing room Ra1 corresponds to the "console 55 of the another image capturing room Ra" in the "case where the radiation image capturing apparatus 1 is already registered in a console 55 of another image capturing room Ra" in the above (2). Thus, when the console $55_2$ associated with the image capturing room Rat registers the radiation image capturing apparatus 1 as described above, the console $55_1$ cancels the registration of the radiation image capturing apparatus 1. Thus, in this case, the cassette ID of the radiation image capturing apparatus 1 is deleted from the registration list of the console $55_1$.

As described in the above (2) that "only when the console 55 (console $55_2$ in the above case) registers the radiation image capturing apparatus 1", even when the attachment notification is transmitted together with the cradle ID of the cradle 53 or the like of the image capturing room Ra2 from the radiation image capturing apparatus 1 or the like, unless the console $55_2$ of the image capturing room Ra2 registers the radiation image capturing apparatus 1 (that is, unless the registration notification is received in the above case), the console $55_1$ does not cancel the registration of the radiation image capturing apparatus 1. That is, the cassette ID of the radiation image capturing apparatus 1 is not deleted from the registration list of the console $55_1$.

Thus, for example, even when the radiological technician or the like carries the radiation image capturing apparatus 1 from the image capturing room Ra1 to the image capturing room Ra2 and attaches the radiation image capturing apparatus 1 to the cradle 53 to register the radiation image capturing apparatus 1, in a case where the console $55_2$ associated with the image capturing room Ra2 does not register the radiation image capturing apparatus 1 due to the radiation image capturing apparatus 1 being not allowed to be registered for licensing violation or the like or due to the failure of registration, the console $55_1$ of the original image capturing room Ra1 does not cancel the registration of the radiation image capturing apparatus 1 and maintains the registration.

Thus, it is possible to accurately prevent the radiation image capturing apparatus 1 from not being registered in any one of the image capturing rooms Ra1, Ra2 and Ra3 and not existing in any one of the image capturing rooms Ra (that is, a sort of missing state) as in the above-mentioned conventional cases.

Modification Example 1

In the above case, after the radiation image capturing apparatus 1 carried into the image capturing room Ra2 is attached to the attachment section such as the cradle 53 or the like (that is, after the attachment notification is transmitted) until the console $55_2$ associated with the image capturing room Ra2 registers the radiation image capturing apparatus 1 (that is, transmits the registration notification), the radiation image capturing apparatus 1 is still registered in the console $55_1$ associated with the image capturing room Ra1.

Thus, in this state, there is a possibility that another radiological technician or the like attempts to specify the radiation image capturing apparatus 1 (here, referred to as a radiation image capturing apparatus 1A) on the console $55_1$ to perform image capturing, and wrongly uses another image capturing apparatus 1 (hereinafter, referred to as a radiation image capturing apparatus 1B) as the radiation image capturing apparatus 1A and performs image capturing in the image capturing room Ra1.

However, in this case, for example, even when the console $55_1$ transmits a wake-up signal to wake up the radiation image capturing apparatus 1A from a sleep state, the wake-up signal does not reach the radiation image capturing apparatus 1A and it is not possible to wake up the radiation image capturing apparatus 1A since the radiation image capturing apparatus 1A is located in the image capturing room Ra2. Furthermore, since the radiation image capturing apparatus 1B does not respond to the wake-up signal transmitted by the console $55_1$, the radiation image capturing apparatus 1B also remains in the sleep state without waking up. When image capturing is performed by using the radiation image capturing apparatus 1B in such a state, the subject is not captured in the image data read by the radiation image capturing apparatus 1B.

Even when the wake-up signal reaches the radiation image capturing apparatus 1A existing in the image capturing room Ra2 and the image capturing request can be received from the console $55_1$, radiation emitted from the irradiation apparatus 52 of the image capturing room Ra1 does not reach the radiation image capturing apparatus 1A in the image capturing room Ra2. Thus, also in this case, the subject is not captured in the image data read by the radiation image capturing apparatus 1A. In this way, image capturing cannot be appropriately performed in any of the above cases.

Thus, in order to prevent such a situation, as shown in FIG. 7, for example, the radiation image capturing apparatus 1 (the radiation image capturing apparatus 1A in the above example) can be configured to prohibit image capturing using the radiation image capturing apparatus 1 after the radiation image capturing apparatus 1 is attached (that is, the attachment notification is transmitted) to the attachment section such as the cradle 53 associated with one image capturing room (that is, the image capturing room Ra2 to which the radiation image capturing apparatus 1 is carried) until the console 55 (the console $55_2$ in this case) associated with the one image capturing room registers the radiation image capturing apparatus 1 (that is, until the registration notification is transmitted).

In this case, the radiation image capturing apparatus 1 (in the above example, the radiation image capturing apparatus 1 which was carried to the image capturing room Ra2 and is currently in the registration processing) can be configured to prohibit image capturing by sending back a signal (see "rejection" in FIG. 7) indicating that the radiation image capturing apparatus 1 is currently in the registration and cannot perform image capturing (that is, rejecting image capturing) even when the image capturing request is transmitted from the console $55_1$ of the image capturing room Ra1 which has not yet cancelled the registration (or even when the image capturing request is transmitted from another console 55 due to any cause).

By such a configuration, for example, while the radiation image capturing apparatus 1 is carried from the image capturing room Ra1 in which the radiation image capturing apparatus 1 has been registered to the image capturing room Ra2 and attached to the attachment section such as the cradle 53 and the console $55_2$ performs the registration processing, even when an image capturing request is transmitted from the console $55_1$ of the image capturing room Ra1 which has not yet cancelled the registration of the radiation image capturing apparatus 1, it is possible to accurately transmit a signal to the console $55_1$ or the like, the signal indicating that the registration is currently performed and the image capturing cannot be performed, and thus prohibit the image capturing (that is, disable the image capturing). Thus, it is possible to accurately prevent the generation of the above-mentioned problems.

Modification Example 2

Separately from the above "Modification Example 1" or together with the "Modification Example 1", after the radiation image capturing apparatus 1 is attached to the attachment section such as the cradle 53 associated with one image capturing room (image capturing room Ra2 in the above example) (that is, after the attachment notification is transmitted) until the console $55_2$ associated with the one image capturing room registers the radiation image capturing apparatus 1 (that is, until the registration notification is transmitted), the another console 55 in which the radiation image capturing apparatus 1 is already registered (console $55_1$ in this case) may control so that the radiation image capturing apparatus 1 cannot be selected as the radiation image capturing apparatus to be used for image capturing.

Modification Example 3

Though not shown in the drawings, during the above period, in a case where the radiological technician or the like attempts to select the radiation image capturing apparatus 1 as the radiation image capturing apparatus to be used for the image capturing on the console $55_1$, for example, the console $55_1$ may notify that the radiation image capturing apparatus 1 cannot be used for the image capturing by displaying, on the display section, or expressing, by sound, that the radiation image capturing apparatus 1 is currently in the registration in another image capturing room and cannot be used.

Even when the console $55_1$ has not yet cancelled the registration of the radiation image capturing apparatus 1, during the above period, the console $55_1$ may not display the radiation image capturing apparatus 1 in a list of radiation image capturing apparatuses 1 which is displayed when the radiological technician or the like selects the radiation image capturing apparatus to be used for image capturing on the console $55_1$, for example.

By the above configurations of [Modification Example 2] and [Modification Example 3], the console $55_1$ of the image capturing room Ra1 cannot perform image capturing using the radiation image capturing apparatus 1 while the radiation image capturing apparatus 1 is carried to the image capturing room Ra2 from the image capturing room Ra1 in which the radiation image capturing apparatus 1 has been registered, the radiation image capturing apparatus 1 is attached to the attachment section such as the cradle 53 and the console $55_2$ performs registration processing, for example. Thus, it is possible to accurately prevent the generation of the above-mentioned problems.

Modification Example 4

There is a case where an image capturing room Ra (hereinafter, referred to as an image capturing room Ra2) does not have the above cradle 53 as the attachment section, a charging cradle 53A is carried into the image capturing room Ra2 (or the charging cradle 53A is provided in the image capturing room Ra2), and the radiation image capturing apparatus 1 is attached to the cradle 53A to be charged in the image capturing room Ra2.

In this case, in the configuration of the embodiment, similarly to the case shown in FIG. 6, the attachment notification including the cassette ID and the cradle ID is transmitted from the radiation image capturing apparatus 1 which is attached to the charging cradle 53A or the cradle 53 to the console $55_2$. The same attachment notification is transmitted to the other consoles $55_1$ and $55_3$.

In this case, the cradle ID of the charging cradle 53A is not written in the list L1 (see FIG. 5A) owned by the console $55_2$. In this way, in the list L1, the identification information (ID) of the attachment section used for registration of the radiation image capturing apparatus 1 is written and the identification information (ID) of an apparatus such as the charging cradle 53A which is not used for the registration of the radiation image capturing apparatus 1 is not written.

In this case, the console $55_2$ determines that the received cradle ID (that is, the ID of the charging cradle 53A) does not belong to the list L1. The consoles $55_1$ and $55_3$ associated with the respective image capturing rooms Ra1 and Ra3 also determine that the received cradle ID does not belong to the list L1.

As mentioned above, in the embodiment, each of the consoles 55 does not determine that the radiation image capturing apparatus is registrable when the cradle ID or the cable ID does not belong to the list L1, and when it is not determined that the radiation image capturing apparatus is registrable, the radiation image capturing apparatus is not registered. Thus, in this case, the console $55_2$ (and the consoles $55_1$ and $55_3$) does not determine that the radiation image capturing apparatus 1 is registrable.

As shown in the above (3), "in a case where the radiation image capturing apparatus 1 is already registered in the console 55 associated with the one image capturing room Ra, when the console 55 does not determine that the radiation image capturing apparatus 1 is registrable, the console 55 does not cancel the registration of the radiation image capturing apparatus 1". Thus, when the radiation image capturing apparatus 1 is already registered in the console $55_2$, the console $55_2$ does not cancel the registration of the radiation image capturing apparatus 1 and maintains the registration.

In such a way, in a case of the [Modification Example 4], even when the charging cradle 53A is carried into the image capturing room Ra2 and the radiation image capturing apparatus 1 is attached to the charging cradle 53A and the attachment notification including the cassette ID or the cradle ID is transmitted from the radiation image capturing apparatus 1 or the cradle 53A, for example, the console $55_2$ does not cancel the registration of the radiation image capturing apparatus 1 on the grounds of the cradle 53A not being associated with the image capturing room Ra2. Thus, it is possible to accurately maintain the registration of the radiation image capturing apparatus 1.

That is, according to the embodiment, even when the radiation image capturing apparatus 1 is attached to the charging cradle 53A and charged in the image capturing room Ra, this does not cause the cancellation of registration of the radiation image capturing apparatus 1 in the console 55.

In a case where the radiation image capturing apparatus 1 can be charged also by a registration cradle 53 (see FIGS. 1 and 4) which is set in the image capturing room Ra, in the embodiment, when the radiation image capturing apparatus 1 is attached to the registration cradle 53 in order to perform the charging, the situation is in the same state as the state shown in FIG. 6.

However, also in this case, the radiation image capturing apparatus 1 is merely registered again in the console 55 in which the radiation image capturing apparatus 1 is already registered, or the console 55 merely maintains the registration since the received cassette ID is already registered in the registration list. Thus, the registration is not cancelled and no problem occurs.

As described above, according to the radiation image capturing system 50 in the embodiment, each of the consoles 55 associated with the respective image capturing rooms Ra is configured to operate in accordance with the above (1) to (3). Thus, it is possible to accurately perform registration and registration cancellation of the radiation image capturing apparatus 1 in the console 55 in each of the image capturing rooms Ra when the radiation image capturing apparatus 1 is carried between the plurality of image capturing rooms Ra to be used.

Thus, for example, in a case where the registration in the console 55 fails in the image capturing room Ra to which the radiation image capturing apparatus 1 was carried, the registration of the radiation image capturing apparatus 1 in the console 55 of the original image capturing room Ra (that is, the image capturing room Ra from which the radiation image capturing apparatus 1 was carried) is not cancelled. Thus, it is possible to accurately prevent the radiation image capturing apparatus 1 from being not located in any one of the image capturing rooms Ra and missing.

Furthermore, in a case where a charging cradle 53A is carried to an image capturing room Ra or a charging cradle 53A in an image capturing room Ra is used and the radiation image capturing apparatus 1 is attached to the charging cradle 53A, it is possible to accurately prevent the console 55 associated with the image capturing room Ra from wrongly cancelling the registration of the radiation image capturing apparatus 1, and thus accurately maintain the registration of the radiation image capturing apparatus 1.

In the embodiment, as shown in FIG. 1, a single console 55 is provided for each of the image capturing rooms Ra, and the image capturing rooms Ra and the consoles 55 are in the 1:1 correspondence. However, as shown in FIG. 8, for example, the present invention can also be applied to a radiation image capturing system 50 in which a single console 55 is associated with a plurality of image capturing rooms Ra (in a case of FIG. 8, image capturing rooms Ra2 and Ra3).

For example, as shown in FIG. 9, in an radiation image capturing system 50 in which a plurality of image capturing rooms Ra and a plurality of consoles 55 are connected via a communication network N, there are cases where a console 55 and an image capturing room Ra are in 1:1 correspondence by the image capturing room Ra being specified on the console 55. Thus, the present invention can also be applied to the radiation image capturing system 50 configured in such a way.

It goes without saying that the present invention is not limited to the above embodiments and such like and modifications can be appropriately made within the scope of the present invention.

What is claimed is:

1. A radiation image capturing system comprising:
   a radiation image capturing apparatus which is portable and reads emitted radiation as image data; and
   a plurality of consoles, each of the consoles having a list including identification information of at least one attachment section which is associated with the console,
   wherein:
   when the radiation image capturing apparatus is attached to an attachment section which is associated with one console among the plurality of consoles, the one console determines whether the radiation image capturing apparatus is registrable, and when the one console determines that the radiation image capturing apparatus is registrable, the one console registers the radiation image capturing apparatus,
   in a case where the radiation image capturing apparatus is already registered in another console among the plurality of consoles, the another console cancels registration of the radiation image capturing apparatus only when the one console registers the radiation image capturing apparatus, and
   each of the consoles (i) determines that the radiation image capturing apparatus is registrable when identification information of the attachment section is included in the list, the identification information of the attachment section being transmitted together with information on the radiation image capturing apparatus from the radiation image capturing apparatus or the attachment section, and (ii) determines that the radiation image capturing apparatus is not registrable when the identification information of the attachment section is not included in the list.

2. The radiation image capturing system according to claim 1, wherein the radiation image capturing apparatus prohibits image capturing using the radiation image capturing apparatus after the radiation image capturing apparatus is attached to the attachment section associated with the one console until the one console registers the radiation image capturing apparatus.

3. The radiation image capturing system according to claim 1, wherein the another console, in which the radiation image capturing apparatus is already registered, performs control to make the radiation image capturing apparatus not selectable as a radiation image capturing apparatus used for image capturing after the radiation image capturing apparatus is attached to the attachment section associated with the one console until the one console registers the radiation image capturing apparatus.

4. The radiation image capturing system according to claim 1, wherein the another console, in which the radiation image capturing apparatus is already registered, notifies that the radiation image capturing apparatus is not usable for image capturing after the radiation image capturing apparatus is attached to the attachment section associated with the one console until the one console registers the radiation image capturing apparatus.

\* \* \* \* \*